(12) United States Patent
Fuller et al.

(10) Patent No.: US 7,775,976 B2
(45) Date of Patent: Aug. 17, 2010

(54) METHOD TO DETERMINE A COAGULATION PROPERTY OF A FLUID

(75) Inventors: Jonathan Andrew Fuller, Amulree (GB); Nasr-Eddine Djennati, Altrincham (GB)

(73) Assignee: Alere Switzerland GmbH, Zug (CH)

( * ) Notice: Subject to any disclaimer, the term of this patent is extended or adjusted under 35 U.S.C. 154(b) by 302 days.

(21) Appl. No.: 11/767,162

(22) Filed: Jun. 22, 2007

(65) Prior Publication Data

US 2008/0160500 A1    Jul. 3, 2008

Related U.S. Application Data

(63) Continuation of application No. PCT/GB2006/000964, filed on Mar. 16, 2006, and a continuation of application No. PCT/GB2005/005076, filed on Dec. 23, 2005.

(30) Foreign Application Priority Data

Dec. 24, 2004   (GB)   ............................... GB0428386
Mar. 19, 1920   (GB)   ............................... GB0505664

(51) Int. Cl.
G01N 33/86   (2006.01)
(52) U.S. Cl. ................... 600/369; 73/54.01; 73/54.24; 73/54.53; 600/368
(58) Field of Classification Search ............ 73/54.01, 73/54.02, 54.23–54.29, 54.39, 54.41, 64.53; 600/368, 369
See application file for complete search history.

(56) References Cited

U.S. PATENT DOCUMENTS

| | | | | |
|---|---|---|---|---|
| 3,796,088 | A | * | 3/1974 | Gustafsson et al. ........ 73/54.25 |
| 4,005,599 | A | * | 2/1977 | Schlatter et al. ............ 73/54.27 |
| 4,648,262 | A | | 3/1987 | Reis et al. |
| 5,110,727 | A | | 5/1992 | Oberhardt |
| 5,204,525 | A | * | 4/1993 | Hillman et al. .......... 250/252.1 |
| 5,629,209 | A | | 5/1997 | Braun, Sr. et al. |
| 5,698,773 | A | * | 12/1997 | Blom et al. ................ 73/54.18 |
| 6,200,532 | B1 | | 3/2001 | Wu et al. |
| 6,591,664 | B2 | | 7/2003 | Litton et al. |

FOREIGN PATENT DOCUMENTS

| | | |
|---|---|---|
| EP | 0400847 | 12/1990 |
| GB | 1244355 | 9/1971 |
| WO | WO-9506868 | 3/1995 |
| WO | WO-2004109277 | 12/2004 |

OTHER PUBLICATIONS

International Search Report for PCT/GB2005/005076, mailed Jun. 24, 2007.
GB Search Report for GB0428386.7.

* cited by examiner

*Primary Examiner*—David A. Rogers
(74) *Attorney, Agent, or Firm*—Beth E. Arnold, Esq.; Foley Hoag LLP

(57) ABSTRACT

Apparatus and method for analysing a biological fluid sample to determine a disturbance of haemostasis resulting in a change of viscosity.

12 Claims, 7 Drawing Sheets

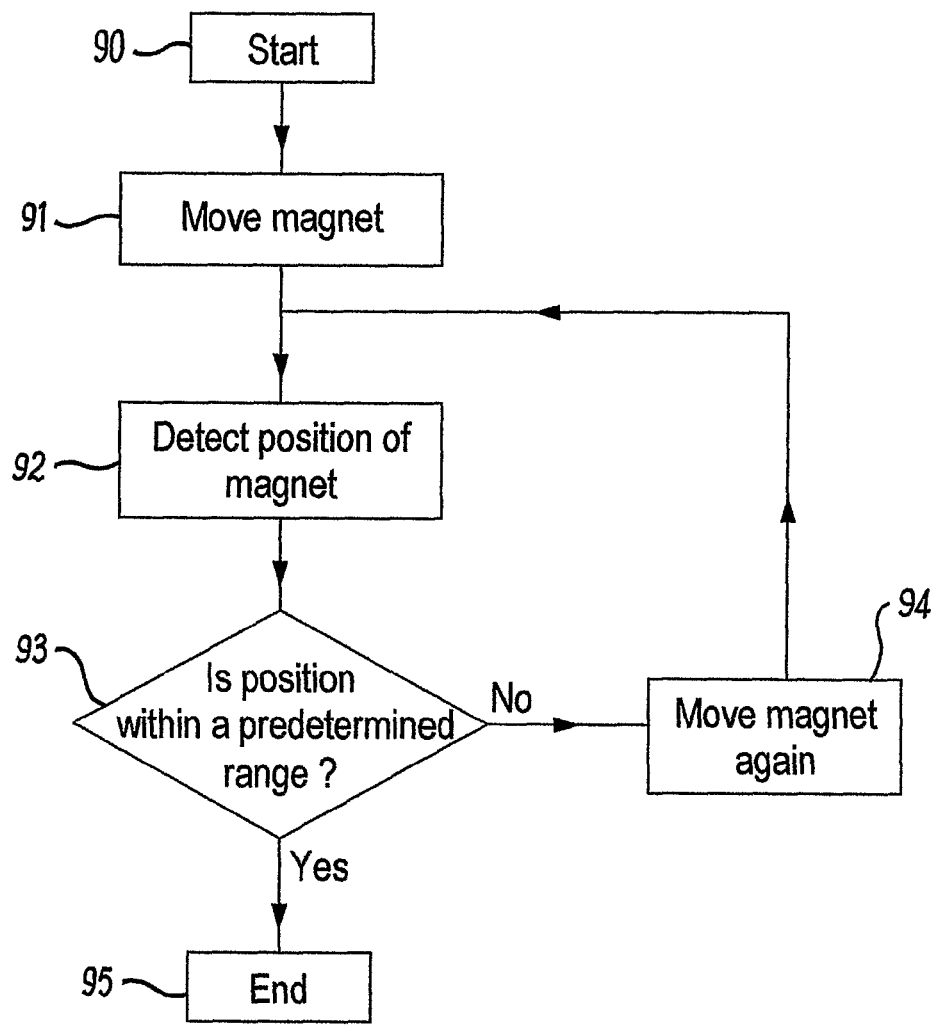

METHOD TO DETERMINE A COAGULATION PROPERTY OF A FLUID

CROSS-REFERENCE TO RELATED APPLICATION

This application is a continuation of International Application No. PCT/GB2005/005076, filed Dec. 23, 2005, which claims the benefit of GB0428386.7, filed Dec. 24, 2004. This application is also a continuation of International Application No. PCT/GB2006/000964, filed Mar. 16, 2006, which claims the benefit of GB0505664.3, filed Mar. 19, 2005. Each aforementioned application is hereby incorporated herein by this reference.

BRIEF DESCRIPTION OF THE DRAWINGS

FIG. 10 shows a flowchart of a method for moving the magnet.

DETAILED DESCRIPTION

Figure 1:
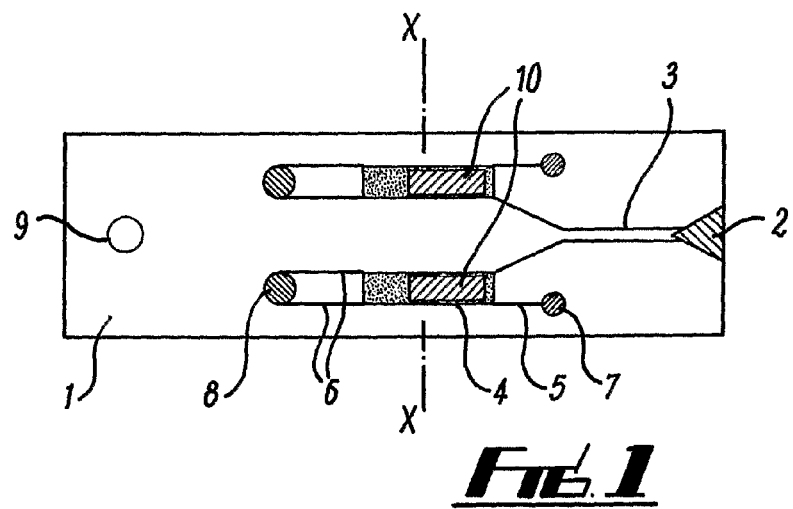
FIG. 1 shows a schematic of a device for use with a meter.

The present disclosure relates to, among other things, an apparatus and a method for analysing a biological fluid sample to determine a disturbance of haemostasis resulting in a change of viscosity.

More particularly but not exclusively there is disclosed an apparatus and method for measuring the coagulation properties of a fluid sample. In embodiments, the method and apparatus may be used to determine the coagulation or prothrombin time (PT) of a sample of blood or plasma. This may be expressed as an Internationalised Normalised Ratio (INR). Other coagulation properties that may be determined include measurement of the degree of platelet aggregation, the rate or amount of clot formation and/or clot dissolution, clot strength, the time required for forming a fibrin clot, the activated partial thromboplastin time (APTT), the activated clotting time (ACT), the protein C activation time (PCAT), the Russell's viper venom time (RVVT) and the thrombin time (TT).

Coagulation of blood in a living body, thrombosis, is one of the leading causes of death world-wide. People who suffer from cardiac or vascular diseases and patients that have undergone surgical procedures are at risk of developing blood clots that may result in life-threatening clinical conditions. Such people are often treated with blood-thinning or anticoagulant drugs such as warfarin or aspirin. However, the amount of anticoagulant in the bloodstream must be maintained at the proper level: too little may result in unwanted clotting whilst too much can result in haemorrhaging with life threatening consequences. As a result, routine coagulation screening tests have been developed in order to evaluate the coagulation status of blood or plasma.

Various apparatus' have been developed for use in the laboratory and as point of care testing (POCT). In addition to this, devices have been developed which allow patients to home-monitor their blood coagulation, such as the InRatio™ monitor (Hemosense) and the CoaguChek™ monitor (Roche) which determine prothrombin time (PT). The CoaguChek™ device is suitable for use with capillary blood wherein a test-device designed to receive a sample of capillary blood is inserted into a test meter. The sample of capillary blood may be conveniently obtained by lancing a finger tip with a lancet.

Many conventional devices for determining a coagulation property of a sample of fluid are large and heavy making them unsuitable to be carried around by the user. A user may be required to test for a clotting time of their own or another's blood on a regular basis in order to ensure good health. Accordingly, there is a need for an apparatus having improved portability.

The rate of coagulation of a sample of fluid is affected by the temperature at which the reaction takes place. A portable device for determining a coagulation property of a sample of fluid may be exposed to a wide range of temperatures thus increasing error in detection of, for example, prothrombin time. For this reason, coagulation devices are provided with a heater which serves to heat the fluid sample to a particular temperature.

A user may be required to test either themselves or a patient on a regular basis using a lancet to draw capillary blood. Such capillary blood samples are typically taken from a convenient bodily extremity such as a fingertip. However, this is a sensitive area containing many nerve endings and obtaining a large sample of blood, i.e. of the order of 25 uL or greater can be painful. Furthermore, it is often difficult to obtain such large quantities without applying significant pressure to the lanced area. This can result in problems such as insufficient quantities of fluid sample being applied to the device requiring the user in many cases to repeat the test.

As the measurement of coagulation is often time based, it is important for such time based measurements to be able to accurately determine the time at which the coagulation reaction starts and a time when coagulation is deemed to have occurred.

Apparatuses and methods disclosed herein may be used in certain instances to determine accurately the time at which a coagulation event takes place in a fluid sample.

Devices disclosed herein may be used in certain instances with a meter for determining the coagulation time of a fluid wherein the test-device has a low volume requirement.

In certain instances, a meter may be provided with a heater and temperature monitor which are able to rapidly heat the fluid sample and to monitor the temperature of the device. The temperature monitor and the heater may be separate entities. The temperature of the device in the region of the chamber and makes the assumption that the temperature of the fluid contained within the chamber is the same as the temperature of the device. In this respect, it is advantageous that the plastic housing of the device is sufficiently thin enough to allow for transfer of heat between the fluid and the device.

In certain instances, a meter for measuring coagulation times may be easily portable and have a low power requirement.

Together, the device and the meter may make up the apparatus. The meter is provided with a device receptacle, and the device is used in conjunction with the meter in order to carry out the test. The device is typically disposable and the meter designed to be reused. Alternatively the meter and device may be provided as a single integral unit, removing the need to insert and position the device.

According to a first aspect, embodiments provide a meter for determining a coagulation property of a sample of fluid, the meter comprising an electromagnetic coil and a device receptacle for receiving a device.

According to a further aspect, embodiments provide a meter for determining a coagulation property of a sample of fluid, the meter comprising a single electromagnetic coil having one or more windings defining an internal space. The device receptacle may be arranged such that the device is capable of being positioned at least partially within said internal space.

According to a further aspect, embodiments provide a device for use with a meter for determining the coagulation status of a fluid sample, the device having at least a fluid chamber containing a magnetic or magnetisable body.

According to a further aspect, embodiments provide a device for use with a meter for determining the coagulation status of a fluid sample, the device having at least two fluid chambers, each containing a magnetic or magnetisable body.

According to a further aspect, embodiments provide for an apparatus for determining the coagulation status of a liquid, the apparatus comprising a fluid chamber for holding a quantity of said fluid, a magnetic body disposed in the chamber and an electromagnetic coil, the electromagnetic coil co-operating with said magnetic body and being arranged in use to provide a magnetic field which causes the body to move to and fro within the chamber.

According to a further aspect, embodiments provide for an electromagnetic coil for use in a meter for determining the coagulation status of a fluid sample, the electromagnetic coil having one or more windings defining an internal space of dimensions such that a device is capable of being positioned at least partially within it.

According to a further aspect, embodiments provide a method of determining the coagulation status of a fluid sample comprising the steps of: providing a sample of liquid in a chamber containing a body and applying a magnetic field to the chamber to cause the body to move to and fro within the chamber through the fluid sample.

According to a further aspect, embodiments provide a meter having a heater and a temperature monitor by which to rapidly heat a fluid sample to a particular temperature or temperature range and to accurately monitor the temperature of said sample.

The device receptacle provided by the meter may have any structure which enables the device to be held accurately and reproducibly within or by the meter. The device receptacle may for example be a cavity in which the device may be placed or inserted. Alternative device receptacle(s) and holder(s) may be employed such as a lock and key mechanism wherein a female feature provided by the device may be arranged so as to cooperate and engage with a corresponding male feature on the test-device and vice-versa.

In the case where a meter having a single electromagnetic coil is provided, the cavity may be arranged so as to be at least partially within the internal space as defined by the one or more windings of the coil.

In the case where an electromagnetic coil having an air core is provided, the electromagnetic coil may be wound about a central axis so as to form an internal air space or air core. The coil may have the form of an open tube. However other forms may be contemplated such as an elongated triangular, ellipsoid, rectangular, square shape and so on, each one defining an internal space.

The device for use with the meter is provided with at least a fluid chamber for receiving a fluid sample. The device may additionally be provided with a fluid application port in fluidic connection with the chamber as well as one of more flow channels in fluidic connection with the fluid application port and chamber. One or more vents may be provided with the device to allow for ingress of fluid sample. The dimensions of the fluid pathways are preferably chosen such that fluid may flow into the chambers under the influenced of capillary force. The dimensions of the chambers may be chosen such that the flow is largely uninfluenced by gravity such that a test may be carried out on a surface that may not be completely horizontal. However, other fluid transporting techniques to transport fluid through the device may be contemplated such as electro-osmotic flow and/or magnetic pumping.

Provided within the chamber is a reagent able to influence the coagulation status of the fluid sample, the nature of which is dependent upon the test to be carried out. For example when the test to be performed is the determination of prothrombin time, the reagent will comprise thromboplastin. Further fluid chambers may be provided containing the same or different reagents which may act as a control to ensure that the test is carried out correctly. Further provided in the or each chamber is a magnetic body. A single magnetic body is preferred although the or each chamber may be provided with one or more magnetic bodies.

The device may have any suitable form including one or multiple magnets. According to an embodiment, the device is provided in the form of an elongated test-strip. The fluidic pathways will largely be sealed from the environment within the device apart from the sample application port and any air vents. The device may be manufactured by lamination of a number of substrates, injection moulding and by other fabrication methods known in the field of microfluidics.

The position of the chamber in relation to the electromagnetic coil is chosen such that in use the magnet passes through a high magnetic field density (i.e. a large number of magnetic field lines) when moving to and fro within the fluid chamber. This creates a high force on the magnet and therefore gives a high power efficiency.

In the case of the electromagnetic coil having a central air core, the chamber is positioned so as to be at least partially within the central cavity defined by the coil so as to correspond to a position having a high field density.

One advantage provided by the use of a hollow electromagnetic coil is that the device may be placed in a region of high magnetic field strength. The device may be placed in close proximity to the coil or at least partially within an internal space defined by the electromagnet, the magnetic body of the device effectively acting as the central magnetic core of the electromagnet. The electromagnet may have a hollow, partially hollow or non-hollow core. Where the core is partially hollow or non-hollow, the core may be partially or completely filled with a non-magnetic or non-magnetisable body. Where the core is partially filled with a non-magnetic or non-magnetisable body, the body should allow for at least partial placement of the device within the internal space as defined by the electromagnet. Placing the device within the hollow core of the electromagnet enables it to be placed in a region of high magnetic field strength, which provides a maximum perturbation of the magnetic field by the magnetic body of the device when in motion giving rise to a large signal. Furthermore the use of a single electromagnet, in particular an electromagnet having a hollow core, reduces the weight, size and power requirements of the device. In the case where the electromagnet is of a high strength, a high field strength may extend beyond the coil itself. In such case it may not be necessary to place the device within the hollow coil, but in close proximity to the coil. However, placement of the device at least partially within the coil is preferred.

In order to obtain a magnet or magnetisable body with a high field strength, it is advantageous to choose a magnetic body having a relatively large size. This enables a chamber of a large size to be used, without effectively increasing the overall blood volume requirement. This provides various advantages with respect to manufacturing.

According to a particular aspect, a device for use with a meter for determining a coagulation property of a sample of fluid, may have at least one cavity for containing a sample of fluid, the or each cavity containing a magnet or magnetisable body for cooperation with the device, wherein the ratio of the volume of the magnet to the volume of the cavity is greater than 0.2. According to a further embodiment it is greater than 0.3. According to yet a further embodiment, it is greater than 0.4. According to yet a further embodiment, it is greater than 0.5.

In order to produce a signal at the magnetic field sensor, it is necessary for the magnetic body to move within the chamber. The greater the distance of travel, the greater the disturbance of the magnetic field and therefore the greater the signal. However, the greater the distance of travel, the larger the volume requirement of the device. In the interests of producing a large signal, it is also desirable to have a large magnetic body having a high magnetic field. However, the larger the body, the less distance is available for travel within the cavity. Given that it is desirable to provide a device having a low volume requirement, there is an optimal range of distance or movement gap to be travelled by the magnetic body as it moves in a to and fro motion within the chamber. The movement gap between the body and walls of the chamber may be between 300 and 600 µm. According to a further embodiment, the movement gap is between 450 and 550 µm. According to yet a further embodiment, the range is between 490 and 510 µm.

Similarly in the interests of optimising the volume requirements of the chamber and the magnetic body, it is desirable to have a clearance gap between a side of the magnet and a wall of the corresponding cavity in a direction transverse to the movement direction wherein said gap is between 50 and 150 µm. According to a further embodiment, the gap is between 75 and 125 µm. According to a further embodiment, the gap is between 95 µm and 105 µm. According to a particular example, the gap is 100 µm.

Movement and/or position detectors may be provided to detect movement and/or position of the body within the chamber. Such a detector may include a magnetic field sensor such as a Hall Effect sensor, magnetorestrictive sensor, search coil or any other apparatus for detecting a change in magnetic field. In an embodiment at least one sensor is provided, each sensor associated with a respective chamber. In operation the magnetic field measured by the sensor will, amongst other things, be affected by the position of the body relative to the sensor. Thus, the output of a sensor can be used to determine position and/or movement of the body in the chamber. The sensor may also respond to the rate of change of magnetic field detecting motion.

The magnetic body of the device is preferably chosen to have a high field density, i.e. a high field strength per unit volume. A high field density imparts a high residual energy into the magnet thus reducing the power requirements needed to enable the magnet to move to and fro within the chamber. This allows for an electromagnetic coil of low field strength to be used which reduces the power requirements of the device. The use of an electromagnetic coil of low magnetic field strength with respect to the magnetic body also gives a high signal to noise ratio. A further advantage provided by this arrangement is that it reduces the need to reproducibly and accurately locate the device with respect to the magnetic field sensor. This in turn allows for a greater tolerance for the device locator and therefore lower manufacturing costs.

The shape, energy density and weight of the magnetic body are important parameters to consider. The weight of the magnet affects its inertia and the higher the weight the higher the energy required to make it move. Conversely, the higher the energy density of the magnet, the more energy it contains and thus less power is required (i.e. from the electromagnet) to make it move. The length will also have an effect on the energy density profile. The field density of the magnet field around the magnet is typically least near its centre and increases towards its pole pieces. The rate of increase in the magnetic field along the length of a magnet is inversely proportional to its length. Thus for two magnets of different lengths having the same overall field density, the shorter magnet will have a greater rate of change in field density along its length than the longer magnet. This is an important consideration as for example, use of a magnetic field sensor such as a Hall Effect sensor, measures the extent or magnitude of the field at any particular time as opposed to measuring the total field. Thus a shorter magnet will give a greater signal at a Hall Effect sensor than a longer magnet even though the magnets might have the same overall field density. The thickness of the magnet will also affect the signal as measured by the sensor. A thin magnet or thin section of the magnet will give rise to a high field density, whereas a thick magnet or thicker section thereof will give rise to a lower field density at that particular part. However, a thin magnet may have less overall mass which will result in a lower field density. The overall shape and aspect ratio of the magnet may also have an affect on the field density. For example a rectangular shape will give rise to a certain energy density profile along its length and a certain energy profile at its pole faces. A magnet shaped like a rugby ball, will give rise to a different energy density profile than would be the case with a rectangular body. Furthermore, the energy density at the ends (poles) of the rugby-ball shaped magnet would be very high, due to the low area of the face at the respective poles. Thus any reference to the field strength at the face of the magnet refers to the overall or average field strength. The aspect ratio of the magnet is also an important consideration. The inventors have shown that an aspect ratio of less than 2:1 (length: width) may result in the magnet twisting in the chamber when subjected to the magnetic field of the electromagnet. An aspect ratio of 3:1 or greater provides a magnet which is suitable for use in a coagulation device.

According to a further aspect, a device for determination of a clotting event may have a chamber containing a magnetic or magnetisable body, wherein the aspect ratio (namely the width to thickness) is greater at the centre of the magnet than at its respective pole pieces (ends).

According to yet a further aspect, a device for determination of a clotting event may have a chamber containing a magnetic or magnetisable body which is magnetised along its length, wherein the aspect ratio (namely the length: to width) is greater than 2:1. Preferably it is greater than 3:1.

In general, the energy density of the magnet, shape, material as well as the energy of the magnetic coil should be chosen such that it results in a signal to noise ratio of 90% or greater.

Other or additional detectors for determining the position of the magnetic body may also be provided such as optical, laser, or radio frequency.

According to one embodiment, there is provided an apparatus for determining a coagulation property of a fluid sample, said apparatus consisting of a meter having a solenoid and a device containing a magnetic body provided within a chamber wherein the ratio of the magnetic field strength of the solenoid to the magnetic field at the tip of the magnetic body is at least 1:2. According to an embodiment, the ratio is at least 1:3. According to a further embodiment, the ratio is 1:4 or greater.

Another embodiment provides a device for use with a meter for determining a coagulation property of a sample of fluid, the device containing at least one magnet having a field at the tip or face of greater than or equal to 30 mT. According to a further embodiment, it is greater or equal to 40 mT. According to yet a further embodiment, it is greater or equal to 50 mT.

Yet a further embodiment provides a device for use with a meter for determining a coagulation property of a sample of fluid, wherein the device operates with a sample of fluid of less than 3 µl. Such a drop may be conveniently obtained from capillaries by use of a lancet.

It is a commonly held belief that there is a lower limit of volume of capillary blood samples that may be used for testing of coagulation time due to the high levels of interstitial fluid that exist in such samples which in turn gives rise to errors in the measurement of coagulation time. However, surprisingly the red blood cell count of very low volume samples of capillary blood obtained from fingers is not substantially affected and accordingly accurate coagulation measurements may be performed on easily obtained small quantities of blood.

In order to ensure complete filling of a device for use with a device for determining a coagulation property of a sample of fluid, each cavity of the device has at least one fill channel and a plurality of vent channels. A channel may be provided at each corner of the cavity. Placing channels at each corner of the detection chamber ensures complete filling of the detection chamber with reduced likelihood of formation of air gaps; this ensures consistent coagulation detection results.

The device may also be provided with means such as one or more one way capillary stops which serve to ensure that the fluid sample having once entered the chamber, is not forced out of the chamber by the to and fro movement of the magnetic body.

Further embodiments provide a method for determining a coagulation property of a sample of fluid whereby the magnet is caused to move in a to and fro fashion through the fluid present in the chamber. The amplitude of the signal for example obtained from a Hall Effect sensor, is dependent upon the rate of movement of a magnet. As the rate of travel of the magnetic body through the fluid starts to decrease, the amplitude starts to decrease. The coagulation time may be considered as the time for complete cessation of movement of the magnetic body or when the amplitude of the signal has decreased to below a certain threshold.

In addition an initial mixing phase at a first frequency can precede a measuring phase at a second frequency to improve fluid homogeneity.

Furthermore, by causing the magnet to move to a predetermined position once a fluid starts entering the device, consistent filling of the chamber may be achieved by ensuring a defined capillary flow around the magnet.

The energy supplied to the electromagnetic coil may be in the form of pulses, causing the magnet to effectively move within the chamber in the form of small pulsed movements. This has been shown to result in a linear movement of the magnet and helps to prevent twisting of the magnet causing it to stick to or become lodged within the chamber which may occur if larger amounts of energy are supplied to the magnet. The number of pulses per translation of the magnet (i.e. a complete to or fro movement) may be constant or it may vary. For example, once the sensor has detected that the magnet has arrived at the end of the chamber, it may signal the meter to stop delivering energy pulses to the coil, thus reducing the energy requirements of the meter. The polarity of the magnetic coil is thereafter reversed, and electrical pulses are once-more applied to the coil to allow the magnet to travel back through the chamber. A time interval may be applied between each or some of the to and fro movements, namely so that the magnet effectively rests, and this time interval may vary or be constant. A time interval may be useful for example to give the sample an opportunity to develop a clot. The meter may have pre-set time intervals. Alternatively, the duration and number of time intervals might be determined by the measurement process itself, for example by a feature of the measurement signal. As the fluid starts to clot, a larger number of pulses may be required to move the magnet from one end of the chamber to the other. The meter may measure the energy required to move the magnet over a fixed distance or measure the distance moved by application of a pulse of a fixed energy. When carrying out a measurement, the magnet may travel the entire distance of the chamber or a partial distance.

A device for use with a meter for determining a coagulation property of a sample of fluid contains a detection chamber for accepting a fluid sample, the detection chamber also containing a magnet which may be used to stir the fluid sample. Stirring is not necessarily a prerequisite for measurement, but can be advantageous. If the detection chamber is filled with a substance other than a sample of fluid, or if the fluid sample in the detection chamber contains air, this can have a very detrimental impact on the accuracy of any measurement made. Furthermore, measurement accuracy can be prejudiced by non-homogeneity of the coagulation reagent within the fluid; a mixing phase can advantageously mix the reagent with the fluid sample in the chamber.

Embodiments provide a device for use with a meter for determining a coagulation property of a sample of fluid, said device having at least one cavity for containing a sample of fluid, the or each cavity containing a magnet or magnetisable body for cooperation with the device, wherein the ratio of the volume of the magnet to the volume of the cavity is greater than 0.4.

The ratio of the volume of the magnet to the volume of the cavity may be greater than 0.5. The strip may be arranged to receive an amount of sample comprising less than 3 µl. Alternatively, the strip may be arranged to receive an amount of sample comprising less than 1 µl. In a further alternative, the strip is arranged to receive an amount of sample comprising 0.7 µl.

The or each cavity may be arranged to receive an amount of sample comprising less than 3 µl. In an alternative, the or each cavity may be arranged to receive an amount of sample comprising less than 1 µl. In a further alternative, the or each cavity is arranged to receive an amount of sample comprising 0.7 µl.

In a further embodiment, the cavity is arranged for movement of the magnet in a movement direction, wherein a clearance or capillary gap between a side of the magnet and a wall of the corresponding cavity is formed in a direction transverse to the movement direction. In an alternative the clearance or capillary gap is between 75 and 125 µm. In an alternative, the clearance or capillary gap is between 95 µm and 105 µm. In another alternative, the clearance or capillary gap is 100 µm.

In an embodiment, the cavity is arranged for movement of the magnet in a movement direction, and wherein a movement gap between a side of the magnet and a wall of the corresponding cavity is formed in the movement direction.

In another embodiment, the movement gap is preferably between 450 and 550 µm. In an alternative, the movement gap is more preferably between 490 µm and 510 µm. In a further alternative, the movement gap is most preferably 500 µm.

Further embodiments provide a fluid sample strip for use with a device for determining a coagulation property of a sample of fluid, said strip having at least one cavity for containing a sample of fluid, the or each cavity containing a magnet for cooperation with the device, the strip being arranged to receive a sample comprising less than 3 µl. In an alternative, the strip is arranged to receive a sample comprising less than 1 µl. In a further alternative, the strip is arranged to receive a sample comprising 0.7 µl.

Further embodiments provide a fluid sample strip for use with a device for determining a coagulation property of a sample of fluid, said strip having at least one cavity for containing a sample of fluid, the or each cavity containing a magnet for cooperation with the device, the or each cavity arranged to receive a sample comprising less than 3 µl. In an alternative, the or each cavity is arranged to receive a sample comprising less than 1 µl. In a further alternative, the or each cavity is arranged to receive a sample comprising 0.7 µl.

Further embodiments provide a fluid sample strip for use with a device for determining a coagulation property of a sample of fluid, said strip having at least one cavity for containing a sample of fluid, the or each cavity containing a magnet for cooperation with the device, wherein the cavity is arranged for movement of the magnet in a movement direction, wherein a clearance or capillary gap between a side of the magnet and a wall of the corresponding cavity is formed in a direction transverse to the movement direction.

In an alternative, the clearance or capillary gap is preferably between 75 and 125 µm.

In an alternative, the clearance or capillary gap is more preferably between 95 µm and 105 µm.

In an alternative, the clearance or capillary gap is most preferably 100 µm.

Further embodiments provide a fluid sample strip for use with a device for determining a coagulation property of a sample of fluid, said strip having at least one cavity for containing a sample of fluid, the or each cavity containing a magnet for cooperation with the device, wherein the cavity is arranged for movement of the magnet in a magnet direction and wherein a movement gap between a side of the magnet and a wall of the corresponding cavity is formed in a direction parallel to the movement direction.

In an alternative, the two opposing sides of the magnet are in planes perpendicular to the movement direction.

In an alternative, the movement gap is preferably between 450 and 550 µm.

In an alternative, the movement gap is more preferably between 490 µm and 510 µm.

In an alternative, the movement gap is most preferably 500 µm.

Further embodiments provide a device for determining a coagulation property of a sample of fluid, the device comprising an electromagnetic coil and a strip receiving cavity for receiving a fluid sample strip, wherein at least a portion of the strip receiving cavity is disposed within the electromagnetic coil.

Further embodiments provide a meter for use with a device for determining a coagulation property of a sample of fluid, the meter comprising an electromagnetic coil having a hollow internal core and a device receiving means for receiving a device.

In an alternative, the strip receiving cavity device receiving means is located in a position so as to enable the device to be disposed at least partially within the internal space defined by the electromagnetic coil.

In an alternative, said electromagnetic coil has an axis and the strip receiving cavity is provided along said axis.

In an alternative, said electromagnetic coil has a core volume and the strip receiving cavity is provided within the core volume.

Further embodiments provide a meter for determining a coagulation property of a sample of fluid, the device comprising a strip receiving cavity for receiving a fluid sample strip, a heating element for maintaining the strip receiving cavity at a predetermined temperature, and a temperature sensor for monitoring the temperature of the fluid sample device.

In an alternative, said heating element is a resistive coil.

In an alternative, said heating element comprises a printed pattern of resistive carbon ink.

In an alternative, said heating element is a Peltier device arranged to heat said cavity.

In an alternative, a polarity of a voltage applied to the Peltier device may be reversed so as to cool the device receiving cavity to the predetermined temperature.

In an alternative, the predetermined temperature is 37° C.

Further embodiments provide a method for determining a coagulation property of a sample of fluid, said method comprising maintaining a sample of fluid in a cavity at a predetermined temperature.

Further embodiments provide a device for use with a meter for determining a coagulation property of a sample of fluid, said device having at least one cavity for containing a sample of fluid, the or each cavity containing a magnet for cooperation with the device, the or each magnet having a minimum field strength at the tip of 50 mT.

In an alternative, the or each magnet has a minimum field strength at the tip of 55 mT to 65 mT.

In an alternative, the or each magnet has a minimum field strength at the tip of 60 mT.

In an alternative, said magnet comprises an NdFe$_3$B magnet.

Further embodiments provide a strip for use with a device for determining a coagulation property of a sample of fluid, said strip having at least one cavity for containing a sample of fluid, the or each cavity containing a magnet for cooperation with the device, the or each cavity further having a plurality of gas trap points, wherein each at least one cavity has a channel connected thereto at each gas trap point.

In an alternative, at least one of said channels is a fill channel.

In an alternative, at least one of said channels is a vent channel.

In an alternative, each gas trap point is a corner of the or each cavity.

In an alternative, the cavity is substantially cuboid in shape.

Further embodiments provide a device for determining a coagulation property of a sample of fluid, the device comprising one optical sensor for detecting both a first event and a second event.

Further embodiments provide a method for determining a coagulation property of a sample of fluid, comprising causing oscillation of the at least one magnet, wherein said oscillation comprises a first oscillation within a first frequency range for a first period of time.

In an alternative, the first event is a fluid entry event.

In an alternative, wherein the second event is a chamber full event.

In an alternative, the optical sensor is arranged to interrogate both a fill channel and a vent channel of a chamber.

In an alternative, the optical sensor is arranged to detect a change in transmission characteristics of the fill channel and the vent channel.

In an alternative, the optical sensor is arranged to detect a reduction in transmission characteristics of the fill channel and the vent channel caused by fluid entering each of said channels.

Further embodiments provide a fluid sample strip for use with a device for determining a coagulation property of a sample of fluid, said strip having at least one locating feature arranged to interact with a corresponding locating component of the device.

In an alternative, the locating feature is a recess in a surface of the fluid sample strip.

In an alternative, the locating feature is a hole in the fluid sample strip.

A schematic of a device is shown in FIG. 1. The device preferably comprises a lower layer 12 which is shaped and a lid 13. The lower layer 12 illustrated is 40 mm in length by 8 mm wide with a thickness of 0.8 mm. The lower layer 12 is shaped so as to have a plurality of features present in a face thereof forming a top surface for the assembled device.

By way of example, the features of the lower layer of the schematic device illustrated in FIG. 1 will now be described. A triangular sample application feature 2 has a depth of 0.3 mm and is joined to at least one, in this example two, inlet channel 3 having a depth of 0.15 mm and a width of 0.3 mm. Each inlet channel 3 is in turn connected to a corner of an entry end of one of two adjacent detection chambers or cavities 4. The detection chamber 4 has a length of 3.5 mm, a width of 1.2 mm and a depth of 0.34 mm. A plurality of vent channels 5, 6 are joined to the detection chamber, the vent channels have a depth of 0.15 mm and a width of 0.15 mm. One vent channel 5 is shown at the entry end of the detection chamber 4 and two vent channels 6 are shown at an exit end of the detection chamber 4 at respective corners, allowing venting of gas traps, wherein said entry end of said detection chamber 4 is opposite the exit end.

FIG. 1 shows a device comprising two detection chambers. These detection chambers are separated by 4.8 mm as measured from the respective centres of the chambers. The separation of the chambers should be such that the magnetic signal associated with the magnet in one chamber does not have or has minimal effect on the Hall Effect sensor associated with another chamber and vice-versa. The optimal separation of the chambers will be determined by factors such as the size and field strength of the magnetic bodies.

It should be noted that a channel is proved at each corner of the detection chamber 4 which has a cross section substantially rectangular in shape and has a small but finite depth in a direction perpendicular to the plane of said cross section. It should further be noted that the fill and vent channels have a depth identical to that of the detection chamber 4. However, the fill and vent channels may have a depth different to that of the detection chamber 4. For example, the fill and vent channels may have a depth between 0.15 mm and 0.1 mm. The depth of the fill and vent channels is preferable consistent along the length of the channel.

A plurality of vents 7, 8 are incorporated into the lower layer, each vent channel 5, 6 being joined to a vent 7, 8 respectively. In the schematic device shown, two vent channels 6 exit a detection chamber 4 and terminate at a common vent 8. The vents 7, 8 comprise circular recesses in the top surface of the lower layer having a diameter of 1 mm and a depth of 0.4 mm. The device further comprises a locating hole 9 which passes through the device; this is discussed in more detail below. In addition, capillary breaks are provided at the junction of the vent channel and the vent (not shown). Thus fluid sample is able to pass along the vent channel as far as the capillary break.

One way stop features are provided to ensure that when reagent is placed in the chamber in liquid form it remains within the chamber until it is dried. However when blood is required to flow into the chamber, the stop does not impede its process The injection moulded lower layer is treated in a plasma chamber so as to produce a hydrophilic layer on the top surface and micro-features of the lower layer. Then a commercially available thromboplastin solution is deposited into each detection chamber 4 of the lower layer. Preferably, each detection chamber 4 contains at least 0.4 µl of thromboplastin solution. The thromboplastin solution is subsequently dried.

The detection chamber is designed to accommodate a fluid sample for testing. The volume of blood required for a test is dependent upon the internal dimensions of the device and the external dimensions of each magnet 10. This volume can be less than 3 µl. In particular it is between 3 µl and 0.1 µl. More preferably, it is between 3 µl and 0.5 µl. Most preferably, it is between 2.75 µl and 0.75 µl. Preferably the volume includes both the volume of the detection chamber and the vent and fill channels.

Each detection chamber 4 of the device contains a neodymium magnet 10. The magnet 10 may comprise $NdFe_3B$. Each neodymium magnet 10 illustrated in FIG. 1 has dimensions of 3 mm by 1 mm by 0.25 mm. The detection chamber 4 illustrated in FIG. 1 has dimensions of 3.5 mm by 1.2 mm by 0.34 mm. Accordingly, the volume of fluid contained by the detection chamber is 0.7 $mm^3$ or 0.7 µl. The ratio of magnet size to detection chamber size is 0.53.

The magnetic body preferably has a high magnetic field strength. However, it has been found that during manufacture of the device, it is difficult to place and retain such high strength magnets in the chamber. This is particularly so when the device has more than one chamber in close proximity to each other, each containing a magnet, as the magnets have a tendency to jump out and stick together. This problem may be overcome by placing a metallic body in the chamber, providing an upper laminate to seal the chamber or at least partially block it, and subsequently magnetising the metallic body to the required field strength in-situ. The presence of the upper laminate prevents the magnetic body from leaving the chamber and enables chambers to be placed in close proximity to each other. It also provides a convenient method of mass-manufacture of such devices and allows other metallic structures which are capable of attracting the magnetic body to be placed in close proximity to the device. Thus a method of manufacturing a device may include the steps of: providing a metallic body capable of being magnetised within a chamber, restricting any movement of the metallic body to within the chamber and subsequently magnetising the metallic body whilst it is present within said chamber.

Each magnet may be chosen of a size such that it substantially fills each detection chamber. This ensures that a high field strength and provides a further advantage that only a small amount of fluid sample is required to fill the chamber. Furthermore substantially all of the fluid in the detection chamber is agitated during testing.

Further, each magnet 10 is sized relative to the detection chamber 4 such that there is a clearance or capillary gap surrounding the magnet when in the detection chamber so as to encourage detection chamber filling and ensure complete filling of the detection chamber. The above dimensions provide a capillary gap of 100 µm around the magnet which is appropriate for this purpose. Similarly, a 500 µm end gap is provided, presenting an optimum value between allowing sufficient magnet movement so as to provide a reasonable signal from the magnetic field sensor 24 yet still allow sufficient capillary effect to ensure filling of the detection chamber without air bubbles. A further advantage is that larger chamber may be employed without compromising the low volume requirement of the device. Furthermore, provision of a large chamber and a large magnetic body enables the manufacturing process to be carried out more easily.

Each magnet 10 preferably has a field strength greater than 50 mT, more preferably 60 mT at the tip (i.e. at the extremity of the magnet at its respective north and south poles).

Figure 2:
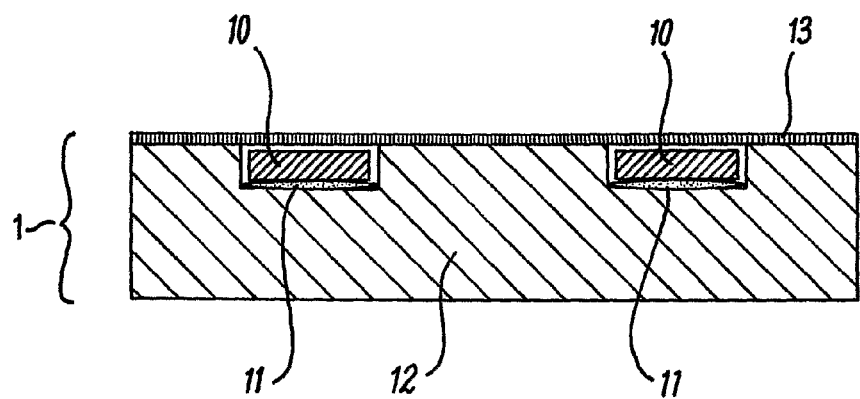
FIG. 2 shows the device in cross section through X-X of FIG. 1.

FIG. 2 shows the completed device in cross section through X-X of FIG. 1. Each detection chamber 4 of the completed device contains both a reagent 11, for example a clotting agent such as thromboplastin, and a magnet 10. The device 1 is shown as comprising the injection moulded lower layer 12, thromboplastin 11, at least one neodymium magnet 10 and a laminate lid 13 bonded to the lower layer 12.

Figure 3:
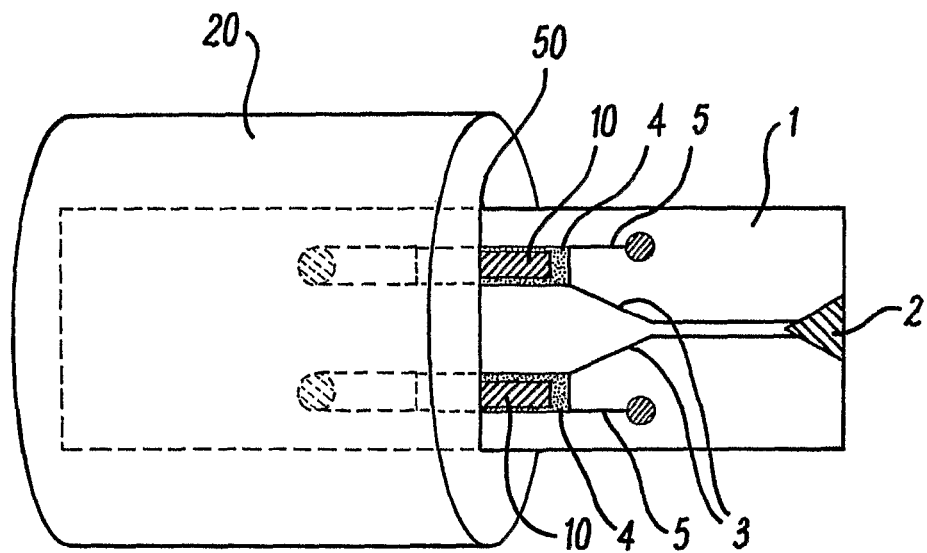
FIG. 3 shows a meter for use with the device.
Figure 4:
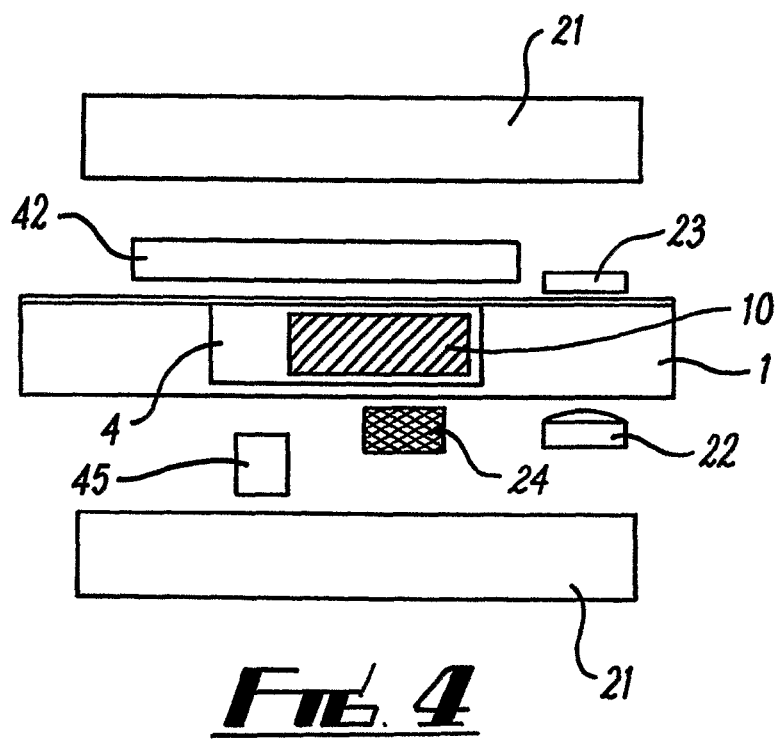
FIG. 4 shows a cross-section of a device inserted into a meter.

An electromagnet 20 forming part of a meter for use with device 1 for detecting a clotting event in a sample fluid is shown in FIGS. 3 and 4. The device may be inserted into the hollow core 50 of the electromagnet. When the device is in the use position, each magnet 10 in each detection chamber 4 may be positioned inside the hollow core of the electromagnet 20.

A female feature provided by the device may be arranged so as to cooperate and engage with a corresponding male feature on the meter. Alternatively, a male feature may be provided by the device and arranged so as to cooperate and engage with a corresponding female feature on the meter.

The magnets 10 have a north-south magnetic pole axis which is parallel to the north-south axis of the electromagnet. The magnets 10 are preferably orientated in the detection chamber 4 such that the end having a north pole is arranged at an end of the detection chamber proximal to the fill channel. Accordingly, a known field may be applied to the device in order to move the magnets 10 to a particular end of the detection chambers 4. By magnetising the material in the strip it is further ensured that the magnets move in the same direction when the electromagnet is energised.

FIG. 4 shows a cross sectional view of the meter 20 with a device 1 inserted, also in cross section. The meter 20 comprises a conducting coil 21 at least one Hall Effect sensor 24 arranged to detect the position of a magnet 10 in each detection chamber 4. The meter 20 also comprises at least one optical sensor 22, 23 these optical sensors preferably comprise LED light sources and conventional optical transistors. The use of optical sensors and the operation of the optical sensors is discussed in more detail below.

According to one embodiment, the coil 21 has a direct current resistance of 70 ohms and is driven by a 5 V power supply.

The coil 21 may have the form of an open tube. The coil may have a cross-section of any other shape, such as for example: triangular, ellipsoid, rectangular, square, circular, etc.

In the multi-chamber configuration shown, a Hall Effect sensor 24 is provided for each detection chamber 4. The Hall Effect sensor 24 is preferably positioned such that a mid point of a detection area of the Hall Effect sensor is aligned with one end of the magnet 10 when the magnet is centred in detection chamber 4. In addition, a heater 42 and temperature sensor 45 is provided adjacent the chamber.

The meter comprises first optical sensors positioned so as to detect a sample fluid passing each inlet channel 3 of each detection chamber 4 and second optical sensors positioned so as to detect the sample fluid passing along each vent channel 5 when a device is inserted into the meter. Alternatively, second optical sensors may be positioned so as to detect the sample fluid passing along each vent channel 6.

Typically, the magnetic field strength at the device 1 generated by the coil 21 is approximately 15 mT. This is a smaller field than prior art meters and preferably reduces the power consumption of the device, making the device lighter and cheaper to run.

Figure 8:
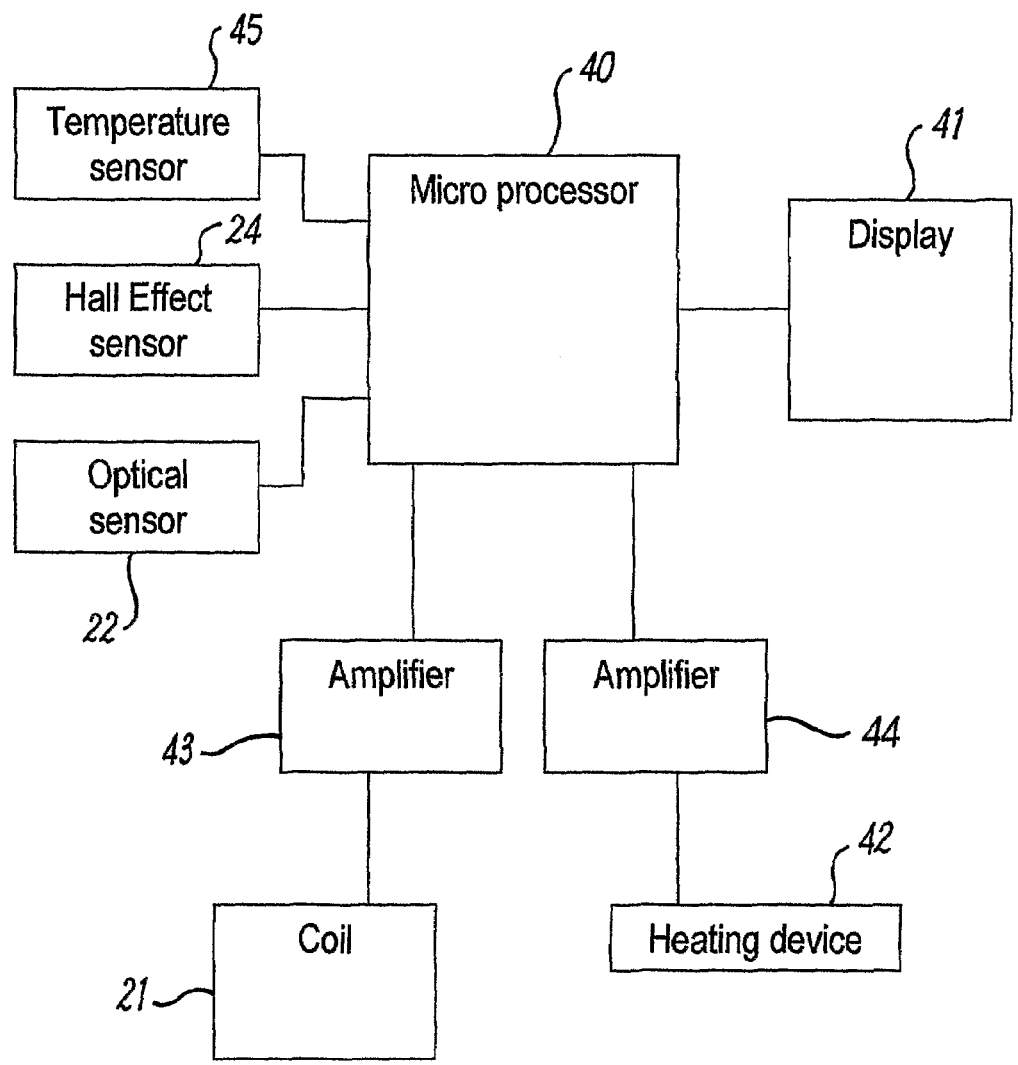
FIG. 8 shows a control circuit for the meter.

FIG. 8 shows a functional block diagram of a control circuit for meter 20. A microprocessor 40 receives inputs from each Hall Effect sensor 24, each optical sensor 22, and a temperature sensor 45. The microprocessor 40 is connected to amplifier 43 and 44 which provide power to coil 21 and the heating element 42 respectively. The microprocessor is further connected to display 41, which may be used to indicate a measurement result to a user. The result may be displayed for example as a clotting time or an International Normalized Ratio (INR) value.

The heating element 42 may comprise a resistive coil which generates heat when a current is passed therethrough. The heating element may comprise a ceramic plate with resistive carbon ink printed on top. Such a heating element may have a resistance of 18 ohms. The heating element 42 may alternatively comprise a Peltier device. The Peltier device functions as a heat pump and is preferably connected to a heat sink.

The heating element 42 preferably functions to heat the device receiving cavity and device to a predetermined temperature as monitored by temperature sensor 45, prior to the device and meter being used to perform a measurement. Temperature sensor 45 may comprise a conventional thermopile arranged to measure infra red radiation emitted by the device. Accordingly, the thermopile is spaced from the device by an air gap; the air gap may be around 3 mm. The thermopile outputs a voltage signal proportional to the temperature of an infra red source the thermopile is directed towards. Preferably, the temperature sensor 45 is directed towards the device 1, rather than the heating element 42; the temperature sensor thus measures the temperature of the device and not the heating element 42, which may be hotter or cooler than the device 1. This reduces error in the temperature measurement of the device caused by variables such as thermal lag, contact pressure, flatness of the device and the like and allows an accurate feedback loop to maintain the temperature at a predetermined desired value. This in turn provides for a more accurate determination of the result as the clotting time is temperature dependent.

The meter 20 displays an indication on display 41 when the device and meter reach the predetermined temperature. The indication may be "ready to test". Upon receiving this indication a user may introduce a fluid sample to the device. If an ambient temperature in which the device and meter are being used is greater than the predetermined temperature, then where the heating element 42 is a Peltier device, a reverse polarity current may be applied to the Peltier device in order to cool the device and device receiving cavity.

The predetermined temperature will depend upon the nature of the test to be performed. In the case of measurement of prothrombin time, the temperature may be chosen to be 37° C.

The operation of the device and meter will now be described with reference to measuring a coagulation time of a fluid sample. A device is inserted into the device receiving cavity of the meter. A fluid sample is placed at the front of the device at sample application feature 2. The fluid moves by capillary action inside the device. The fluid is taken up from the sample application feature 2, along each inlet channel 3 into each detection chamber 4. The sample fluid continues to flow through each inlet channel 3, filling each respective detection chamber 4 and continues to flow out through vent channels 5 and 6. The sample fluid stops flowing when the fluid in the vent channels 5 and 6 reaches capillary breaks 7 and 8 respectively. Placing channels at each corner of the detection chamber ensures complete filling of the detection chamber with reduced likelihood of formation of air gaps; this contributes to ensuring consistent coagulation detection results.

In a preferred embodiment, the fluid moves through the device by capillary action. However, other standard means of transporting fluid into the device may be contemplated such as electro-osmotic flow.

As described above, optical sensors are provided for detecting a sample fluid entry event and/or a detection chamber full event. A sample fluid entry event may be defined as detection of sample fluid in a fill channel of the device. A detection chamber full event may be defined as detection of sample fluid in at least one vent channel of the device.

Upon detecting sample fluid in the inlet channel 3 of the device 1, which defines a fluid entry event, the meter 20 begins timing.

Figure 5:
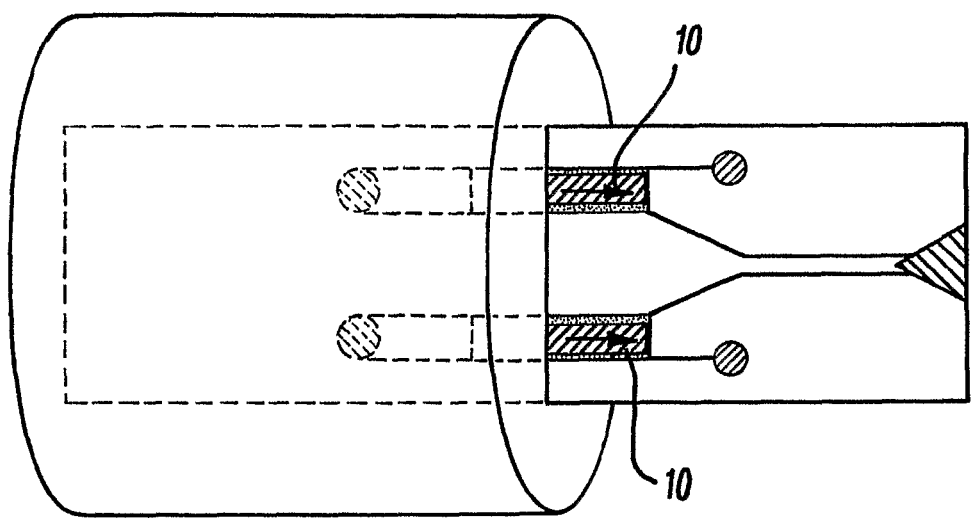
FIG. 5 shows two magnets being positioned within the device.

Also, upon detecting a fluid entry event, a fill signal is applied to the coil 21 to create a magnetic field of a fixed polarity such that the magnets 10 in the detection chambers 4 are repelled away from the coil 21 towards the sample application feature 2 of the device 1, as shown in FIG. 5. This positioning of the magnets during a fill stage ensures reproducible filling of the chamber with fluid sample. Accordingly it is advantageous to fix the magnet in a known position in order to provide consistent fill characteristics for different tests. The fill signal is maintained for 3 seconds after which time the chamber is assumed to be full.

After the fill signal, a mix signal is applied to the coil 21, the mix signal producing oscillating magnetic fields having opposing polarities. The mix signal preferably produces an oscillating magnet field around the coil 21 oscillating at approximately 8 Hz. The mix signal is applied for 5 seconds in order to ensure mixing of the fluid sample and the reagent 11 shown in FIG. 2.

Figure 6:
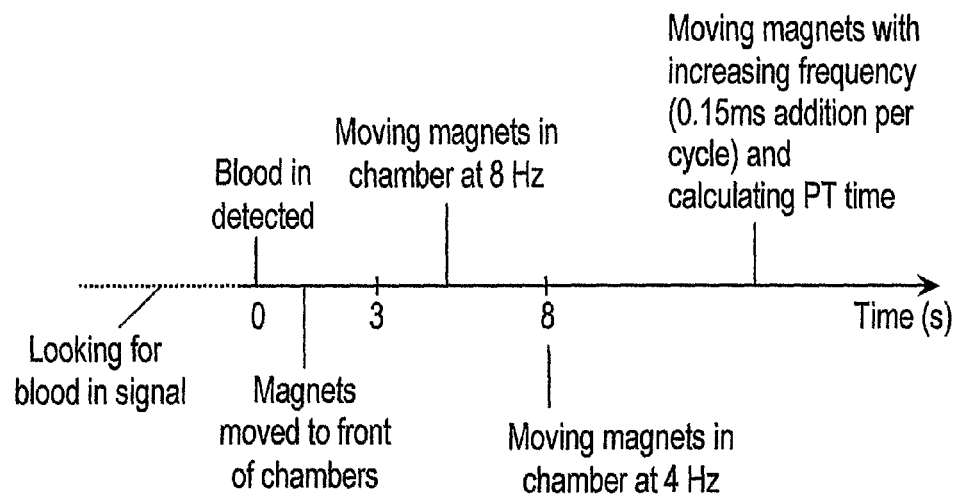
FIG. 6 shows a method of power application to the coil of the meter.

After the mix signal, a measure signal is applied to the coil 21. The measure signal producing oscillating magnetic fields having opposing polarities and initially oscillating at approximately half the frequency of the mix signal. The mix signal preferably produces an oscillating magnet field around the coil 21 initially oscillating at approximately 4 Hz. During the application of the measure signal, the period of oscillation of the magnetic field around coil 21 is preferably increased by 15 milliseconds per cycle. An example of this method of power application to the coil is shown schematically in FIG. 6.

The measure signal is applied to the coil 21 until detection of a coagulation event as described in more detail below.

The coil 21 draws a direct current of 71 mA when connected to 5 V power source. In order to reduce power consumption, the coil is operated at a 50% duty cycle at a frequency of 50 Hz. This reduces the average current consumption to around 35 mA. Further, during any one half cycle the magnet may only be powered for a portion of the half cycle. Current is applied having a first polarity during a portion of a first half cycle and then current is applied having a second polarity for a portion of a second half cycle, the second polarity being opposite the first polarity. For example, if the magnet is oscillating at 2 Hz, then a half cycle has a 250 ms duration. During a first half cycle a signal of a first polarity is applied to the coil for 100 ms, then, during the second half cycle a signal of a second polarity is applied to the coil for 100 ms. Preferably, the signal of a first or second polarity comprises pulsed voltage; the duty cycle of the pulses may be reduced in order to conserve power.

The pulsing of current in opposite directions preferably comprises the application of an alternating voltage source; the alternating voltage source may comprise a square wave signal, a sinusoidal signal, or a triangular waveform signal.

Figure 7:
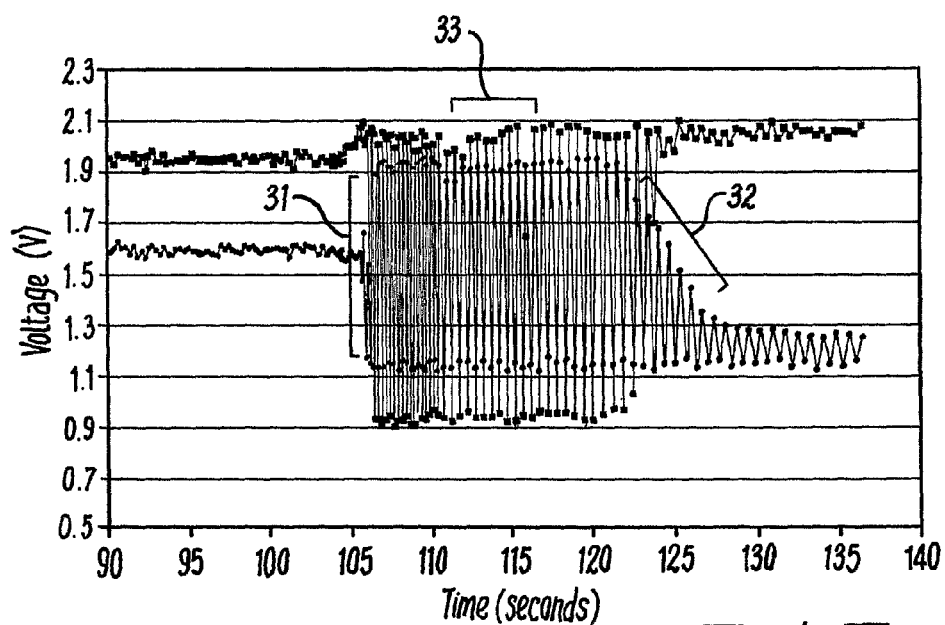
FIG. 7 shows an output signal from each of two Hall Effect sensors during a clotting test.

In order to detect movement of the magnet a signal output from each of the Hall Effect sensors 24 of meter 20 is processed as shown in FIG. 7. A peak amplitude 31 of the signal output from each Hall Effect sensor indicates the motion of the tip of the magnet 10 as it oscillates. The signal output indicates that the magnets perform a reciprocating motion in response to the field applied by the coil 21. As the magnetic body begins to slow indicating that the fluid sample or blood is undergoing a clotting event, the amplitude, and speed of the magnet motion and the corresponding peak amplitude and/or speed of an output signal from the Hall Effect sensor is reduced 32. The magnitude of the voltage after a clotting event has occurred may be an indication of the clot strength and thus this value may be used to determine the clot strength of a particular fluid sample. Furthermore, following a clotting event, the device may also be used to determine the rate of clot dissolution by continuing to cause the magnetic body to move to and fro through the sample. If necessary the magnetic field strength may be initially increased to cause the body to move through the sample.

Each magnet 10 is magnetised along a longest axis in a direction parallel to a direction in which it reciprocates upon application of the alternating magnetic field by coil 21. Accordingly, the magnetic field measured along the length of the magnet is minimum at the centre and maximum at the ends. As the magnet displacement within the detection chamber 4 varies, the output signal from the Hall Effect sensor varies also. Accordingly, it is possible to calibrate the output signal from the Hall Effect sensor 24 to define an amount of displacement of the magnet within the detection chamber 4. The correlation between Hall Effect sensor output signal and magnet displacement is non linear as the magnet tip moves passed the Hall Effect sensor 24. This non linearity is accounted for during calibration.

The displacement is converted to a distance travelled i.e. the end positions of the magnet are subtracted. Therefore this is a direct measure of the distance the magnet has travelled in a given cycle. This value decreases as the clot forms.

A coagulation event may be defined as the time at which the magnet has ceased to move or when it has slowed down to a particular extent. It can readily be determined by measurement of the amplitude of the signal or by the change or rate of change in the signal amplitude. The fluid sample or blood clots, preventing the magnet from moving and can be further defined as a predetermined reduction in Hall Effect sensor output signal amplitude from an average amplitude.

The extent of change in amplitude may be dependent upon factors such as the INR of the blood, the size and shape of the magnet and the ratio or difference of the field strength of the magnet compared to that of the electromagnet. For example, a clotting event may be deemed to have occurred when the signal amplitude is 70% of the average amplitude signal, the average amplitude signal being the average of all the amplitude measurements measured during a particular time frame such as first 5 seconds of measurement.

Alternatively a moving average smoothing may be applied to the magnet motion signal and then an amplitude drop measured.

Figure 9:
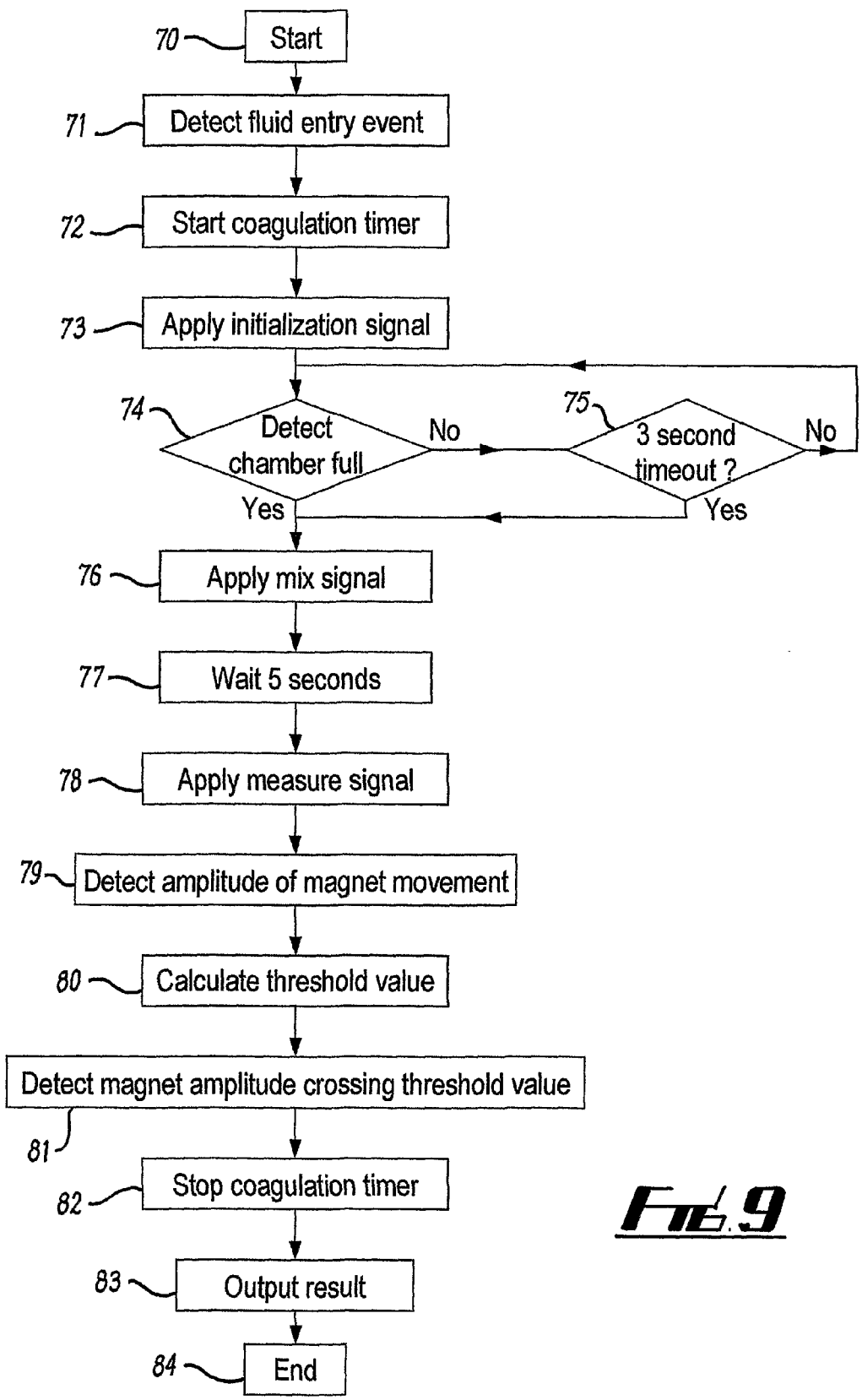
FIG. 9 shows a flowchart of a method for operation of the device.

FIG. 9 shows a flowchart of a method for operation of the apparatus. The method comprises detecting 71 a fluid entry event using the optical sensor 22, 23, which causes the start 72 of a coagulation timer and the application 73 of an initialization signal to the coil 21. The coagulation timer is implemented by microprocessor 40. Upon either: detection 74 of a chamber full signal form another or the same optical sensor 22, 23; or the expiry 75 of a predetermined time out of 3 seconds; the apparatus applies 76 a mix signal to the coil 21 for 5 seconds. After 5 seconds 77 of the mix signal, a measure signal is applied 78 to the coil and the amplitude of the magnet movement is detected 79. A threshold value is calculated 80 from the measured the amplitude of the magnet movement by multiplying the measured value by a fraction such as 70%. The measure signal is applied 78 until the apparatus detects the amplitude of the magnet movement reducing 81 to a value less than the threshold value, which defines the occurrence of a coagulation event. Upon detection of the coagulation event: the coagulation timer is stopped 82; the measure signal is stopped; and the measured coagulation time is output 83 by the apparatus.

FIG. 10 shows a flowchart of a method for moving the magnet, said method comprising: moving 91 the magnet; detecting 92 a position of the magnet; determining 93 whether the detected position of the magnet is within a preferred range; and moving 94 the magnet again if the detected position of the magnet is not within a preferred range.

A method of manufacture of the device shown in FIG. 1 will now be described. The lower layer 1 is preferably formed from polystyrene by injection moulding techniques known in the art. The lower layer illustrated is 40 mm in length by 8 mm wide with a thickness of 0.8 mm. The lower layer is shaped during moulding so as to have the plurality of micro-features present in a top surface.

The injection moulded lower layer is treated in a plasma chamber. The plasma chamber causes a hydrophilic layer to be deposited on the top surface and micro-features of the lower layer.

A commercially available thromboplastin solution is deposited into each detection chamber 4 of the lower layer. The thromboplastin solution may be deposited using a deposition station such as those provided by Horizon Instruments Ltd, UK. Preferably, at least 0.4 µl of thromboplastin solution are deposited in each detection chamber 4. It would be apparent to one skilled in the art that a plurality of other known thromboplastin solutions are appropriate for use in this apparatus.

The deposited thromboplastin solution is dried by passing the lower layer through a heated chamber for 10 min at a temperature of around 65° C. for 4 minutes and then a temperature of around 45° C. for 6 minutes.

Following the deposition of the thromboplastin solution into each detection chamber 4 of the lower layer and the subsequent drying, a neodymium magnet 10 is placed into each detection chamber 4 in the device 1.

The lid is placed on the lower layer and attached thereto. The lid preferably comprises a polystyrene laminate 125 µm thick and is preferably attached to the lower layer by an adhesive. Alternative methods for attaching the lid to the lower layer are possible.

Once the lid is bonded to the lower layer, a 25 W carbon dioxide laser is used to cut through the lid material laminate to enable excess lid material to be removed from the edges of the lower layer. The 25 W laser is also used to pierce the lid above the vents 7, 8 so as to produce venting holes. In use, the venting holes allow air to escape from the detection chamber 4 when sample fluid is introduced to the device 1 at the sample application feature 2.

The arrangement set out herein gives rise to a range of advantages. The use of a strong magnetic material such as $NdFe_3B$ for each magnet 10 in the detection chamber 4 is advantageous for various reasons.

Firstly, a smaller magnetic field is required to be produced by the electromagnetic coil 21 in order to produce a particular propulsion force to drive the magnet 10 through the fluid sample in the detection chamber 4. The coil 21 may thus be smaller and will consume less power so the meter 20 may have a smaller power supply. This is particularly advantageous in embodiments where the meter 20 is portable and is powered by batteries.

Second, a stronger magnet 10 produces a higher signal strength at the Hall Effect sensor 24. Accordingly, a signal to noise ratio of the Hall Effect sensor output is reduced allowing for improved accuracy in detection of a coagulation event.

Positioning the Hall Effect sensor 24 such that it is aligned with one end of the magnet 10 when the magnet is centred in detection chamber 4, maximises a change in magnetic field and accordingly output signal from Hall Effect sensor 24 as the magnet moves from one end of the detection chamber 4 to an opposite end. This also advantageously improves the signal to noise ratio of the signal output by each Hall Effect sensor 24. The Hall Effect sensor in general is positioned as close as conveniently possible to the chamber in order to give the biggest signal.

The two detection chambers shown in FIG. 1 are separated by 4.8 mm as measured from the centres of each chamber.

Positioning of the two chambers adjacent to one another as shown in FIG. 5 and sufficiently close to one another such that the magnetic fields of the respective magnets interact with one another has been shown to stabilise the magnets and stop them from twisting in the chamber when subjected to the magnetic fields of the electromagnet. There are further advantages in placing the chambers close together such enabling the device to be smaller in size and reducing the size of the heating element. However, if the chambers are positioned too close to one another, the magnet in one chamber can interfere with the motion of the magnet in the other chamber as illustrated in FIG. 13. Interference of the motion of one magnet by another may be exhibited as one magnet being attracted to another, causing friction between the magnet and a side of the chamber, impeding the movement of the magnet. Any such interference can potentially give rise to the meter incorrectly indicating a clotting event. There is therefore a minimum separation of the two chambers, wherein the minimum separation may be defined as the minimum distance required such that the magnets do not significantly interfere with the motion of one another so as to cause the meter to incorrectly provide an early indication of a clotting event. Ideally the chambers will be positioned such that the respective magnets do not interfere with the motion of the other. However, some interference is permissible as long as it does not compromise the respective results of the clotting times. The separation between the chambers will also be determined by the magnetic field density of the respective magnets. The larger the magnetic field density, the greater the separation will need to be. Thus there is an optimum separation range of the two chambers, wherein if the chambers are too close the magnets may interfere with the motion of one another to a significant extent and if they are too distant it may result in twisting of the magnets in use and may result in a larger test-strip and the need for a larger heater. For a device having two chambers each having a NdFe$_3$B magnet of dimensions of 3 mm by 1 mm by 0.25 mm and having a field strength of 50 mT at its tip, a separation of 4.8 mm has been shown to provide adequate stabilisation of the magnets without each magnet interfering significantly with the each other. A separation of 4 mm from the respective centres of the chambers has been shown to be unsuitable as the magnets interfere with one another to a significant extent.

The output signal from the magnetic field sensor is proportional of the magnetic field strength. Thus, the absolute position and/or rate of movement of the magnet within the chamber may be derived from the output signal from the Hall Effect sensor 24. In an alternative apparatus, it is thus possible to input only an amount of power into coil 21 required to move the magnet 10 across the detection chamber 4, instead of over driving the coil. The coil 21 is provided with a short duration signal to produce a short duration magnetic field. If the signal output from the Hall Effect sensor does not indicate the magnet is at a measurement extreme, such as at one end of the detection chamber 4, then another short duration signal is applied to the coil 21. If the fluid sample has not coagulated, then the magnet 10 will eventually reach an end of the detection chamber 4 and the process may be repeated with short duration signals applied to coil 21 having an opposite polarity. In this manner only a minimum amount of power is input into the coil 21 to move the magnet 10. This advantageously reduces power consumption of the meter 20. Furthermore such measurement methods may be employed to determine clotting times at high INR's or when the clot is weak. In such circumstances application of a pulse of short duration may make the device more sensitive to detecting a clotting event. Upon coagulation of the fluid sample the magnet 10 is prevented from traversing the detection chamber 4, which is detected by the Hall Effect 24 sensor as described above. Alternatively or additionally the power supplied to the coil may be caused to vary during the measurement.

Applying an excess of power to the electromagnetic coil causes excessive use of energy by the meter. This may cause excessive depletion of any finite power supply such as a battery which can reduce operable life and increase cost of operation. Furthermore, by detecting the position of the magnet during oscillation, only the minimum required energy need be applied to operation, conserving battery power.

In the example described above, the polarity of the magnets 10 is known in respect of their orientation in the detection chamber 4, and accordingly the polarity of field that must be applied to the detection chamber in order to move the magnets into a predetermined position during filling is known. In an alternative, the polarity orientation of the magnets 10 is not known, and so a preliminary fill signal is applied to the coil 21 and the position of the magnet 10 is detected by either Hall Effect sensors or optical sensors. If the magnet is in a desired predetermined position, the fill signal is maintained as described above. If the magnet is not in a desired predetermined position, the polarity of the fill signal is reversed and the position of the magnet 10 is again detected. If the meter does not detect the or each magnet 10 being in a desired position, an error signal is produced.

In the above example, means is provided to detect the position of the magnetic body 10 within the detection chamber 4. In an alternative, a means is provided to detect movement of the magnetic body 10. In operation, the movement measured by the sensor will reduce due to a change in viscosity of the fluid sample brought about by a disturbance in haemostasis.

Alternatively still, at least one optical sensor may be used to detect the position of the or each magnet 10. In operation, a reduction in the frequency of changes in the optical transmission properties of the detection chamber 4 indicates a change in viscosity of the fluid sample brought about by a disturbance in haemostasis. The presence or lack thereof of a magnet 10 at a predetermined position of the detection chamber 4 determines the optical signal measured by the optical sensor.

An alternative arrangement of the at least one optical sensor will now be described. An optical sensor may be provided for each detection chamber, the optical sensor positioned to detect the optical transmission, of both inlet channel 3 and vent channel 5. Upon a first transmission reduction event, fluid is detected in inlet channel 3, and upon a second transmission reduction event, fluid is detected in vent channel 5. Accordingly one optical sensor per chamber can be used to detect both a fluid entry event and a chamber full event.

It should be noted that while specific examples of signals applied to the coil 21 have been described above with reference to duty cycle and frequency, these signals are given by way of example only. The duty cycle of pulses applied to the coil must only be greater than 0% and is determined by the coil and power supply used. The frequency of oscillating signals such as the mix signal and the measure signal applied to the coil 21 are preferably between 1 Hz and 50 Hz.

In the above example, each detection chamber 4 contains a reagent 11. In an alternative, two detection chambers 4 are provided wherein only one detection chamber 4 contains a reagent 11, the other detection chamber 4 acts as a control during the measurement process.

In the above case, the clotting time may be measured from the detected fluid entry event, which may be defined as time zero. An alternative measure of time zero may be measured by programming the meter 20 with a preset delay to account for filling characteristics of the device 1.

Alternatively, meter 20 may detect both a sample fluid entry event and a detection chamber full event and calculate a time zero according to a predetermined algorithm defined from measured filling characteristics of the device 1. Detection of a chamber full event may be used to trigger a transition from applying a fill signal to the coil 21 to applying a mix signal to coil 21 in lieu of the fixed 3 second time described above.

Further, the given example of reduction in the output signal of Hall Effect sensor 24 to determine cessation of magnet reciprocation is given as an example. Alternative methods for determining the cessation of magnet reciprocation may be applied.

A method for determining a coagulation or a clotting property of a sample of fluid is provided whereby the initial viscosity of the fluid sample is accounted for by measuring the amplitude of movement of a magnet located in the fluid sample prior to coagulation and then detecting a predetermined reduction in this amplitude to determine the occurrence of a coagulation event.

We claim:

1. A method for determining a coagulation property of a sample of fluid, comprising:
   causing within the sample oscillation of at least one magnet within a first frequency range for a first period of time;
   causing oscillation of the at least one magnet within a second frequency range different from the first frequency range for a second period of time;
   increasing the period of the second oscillation from an initial second frequency by a fixed time increment per pulse;

measuring an output signal of at least one sensor, the output signal being indicative of a position or motion of the at least one magnet; and determining the coagulation property of the sample based on the output signal.

2. The method of claim 1, wherein said first frequency is greater than said second frequency.

3. The method of claim 1 wherein the fixed time increment per pulse is 0.15 milliseconds.

4. The method of claim 1, wherein the first frequency is between 5 and 12 Hz.

5. The method of claim 1, wherein the first frequency is between 7 and 10 Hz.

6. The method of claim 1, wherein the first frequency is substantially 8 Hz.

7. The method of claim 1, wherein the first period of time is between 2 and 8 seconds.

8. The method of claim 1, wherein the first period of time is between 4 and 6 seconds.

9. The method of claim 1, wherein the first period of time is substantially 5 seconds.

10. The method of claim 1, wherein the second frequency is between 2 and 6 Hz.

11. The method of claim 1, wherein the second frequency is between 3 and 5 Hz.

12. The method of claim 1, wherein the second frequency is substantially 4 Hz.

* * * * *